United States Patent [19]

Turner

[11] Patent Number: 4,597,800
[45] Date of Patent: Jul. 1, 1986

[54] OXO-ALUMINUM COMPLEXES

[75] Inventor: John H. W. Turner, Chapel-en-le-Frith, England

[73] Assignee: Manchem Limited, Manchester, England

[21] Appl. No.: 684,883

[22] Filed: Dec. 19, 1984

Related U.S. Application Data

[63] Continuation-in-part of Ser. No. 269,218, Jun. 2, 1981, abandoned, which is a continuation-in-part of Ser. No. 144,554, Apr. 28, 1980, abandoned.

[30] Foreign Application Priority Data

Apr. 30, 1979 [GB] United Kingdom ............... 7915027
Apr. 24, 1980 [EP] European Pat. Off. ........ 80301329.1

[51] Int. Cl.$^4$ ............... C09D 3/26; C07F 5/06
[52] U.S. Cl. ............... 106/264; 556/40; 556/183; 556/179; 106/310
[58] Field of Search ............ 260/448 R, 448 AD, 414; 556/40, 183; 528/9; 106/18.14, 264, 310; 523/148; 525/523

[56] References Cited

U.S. PATENT DOCUMENTS

| | | | |
|---|---|---|---|
| 4,075,178 | 2/1978 | Turner | ............... 260/448 AD X |
| 4,090,886 | 5/1978 | Turner . | |
| 4,132,724 | 2/1979 | Turner | ............... 260/448 AD |

FOREIGN PATENT DOCUMENTS

| | | |
|---|---|---|
| 85300 | 12/1955 | Czechoslovakia . |
| 772480 | 4/1957 | United Kingdom . |
| 888666 | 1/1962 | United Kingdom . |
| 907558 | 10/1962 | United Kingdom . |
| 1544405 | 4/1979 | United Kingdom . |

OTHER PUBLICATIONS

Chemical Abstracts, vol. 85, 162045(a), (1976).
Chemical Abstracts, vol. 86, 157161(b), (1977).

*Primary Examiner*—Helen M. S. Sneed
*Attorney, Agent, or Firm*—James R. Thornton

[57] ABSTRACT

Oxo-aluminum complexes prepared by reacting a substituted aluminum alkoxide with a molar deficiency of water or carboxylic acid. The complexes are useful in surface coating compositions based on synthetic resins such as alkyd resins.

12 Claims, No Drawings

OXO-ALUMINUM COMPLEXES

This is a continuation-in-part of my copending application Ser. No. 269,218 filed June 2, 1981, now abandoned, which, in turn, is a continuation-in-part of my earlier application Ser. No. 144,554 filed April 28, 1980, now abandoned.

This invention relates to aluminum complexes and to air drying compositions containing them, in particular surface coatings based on synthetic resins.

BACKGROUND OF THE INVENTION

It is known that aluminum compounds can function as coordination driers in paints and they have been used as replacements for lead driers because of their relatively low toxicity. The preferred aluminum compounds are the alkoxides such as aluminum isopropoxide, higher alkoxides, substituted alkoxides, and the oxo-aluminum compounds.

Oxo-aluminum compounds are generally obtained by reacting optionally substituted aluminum alkoxides with water, monocarboxylic acids, alcohols and/or phenols in the manner disclosed in several prior references such as for example British Patent Specification Nos. 806113, 825878 and 907558. British Specification No. 1001837 discloses oxo-compounds prepared by methods analogous to those described in prior specifications which contain in addition to aluminum atoms, one or more selected hetero atoms such as copper, magnesium, zinc, cadmium, lead, etc.

To effect the condensation reaction one mole of water is used for each two alkoxide groups present and the reaction may be represented as involving the following stages:

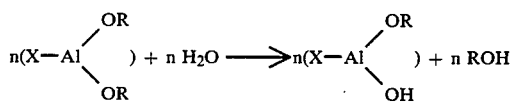

On heating this partially hydrolyzed compound under distillation conditions, inter- and intra-molecular condensation will result in condensation which may be represented as follows:

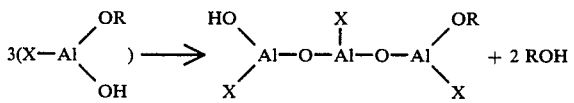

and with further heating:

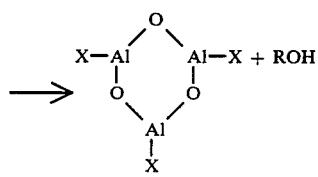

However, in surface coating applications, the usefulness of these aluminum compounds is limited by their excessive reactivity with free carboxyl groups. Other potentially reactive groups are hydroperoxyl, hydroxyl and active methylene groups which may be available in the resin medium but in practice are found to be of lower reactivity. This reaction may be represented as follows for free carboxyl groups:

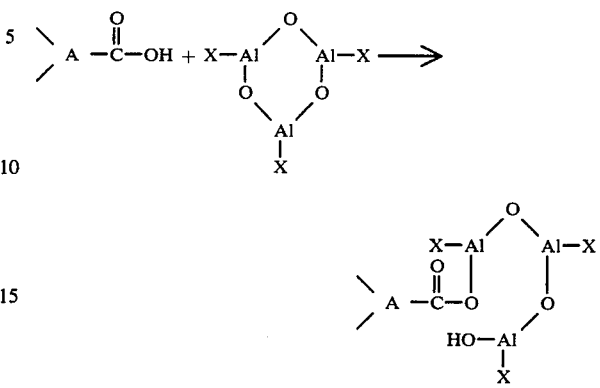

Because of this reactivity, association occurs and tends to increase the molecular weight and hence the viscosity of the medium. This can be countered by dilution with more solvent but the resulting decrease in the solids content causes a diminution in the binding properties and durability of the medium. Therefore, the successful use of such aluminum compounds as driers has been mainly limited to applications such as in printing inks and surface coating applications in which a high viscosity or low solids content is not a disadvantage. The usefulness of aluminum compounds containing alkoxide substituents may also be impaired by the readiness with which such compounds can be hydrolyzed by atmospheric and other sources of water with which they may come into contact. This has also imposed limitations on the applications for which some aluminum compounds and their derivatives are suitable.

British Patent Specification No. 772480 discloses aluminum compounds having the oxo-linkage and alternatively carboxyl and alkoxy substituents on the aluminum atoms which are formed by reacting aluminum alcoholates with a mono-basic organic acid or acid amide substance. It is proposed that the products may be used in the lacquer and varnish industries. However, these products would not be eminently suitable as driers in surface coating formulations containing drying oils or resins as the number of alkoxide groups present on the aluminum compound would make the products particularly sensitive to hydrolysis by atmospheric moisture.

Similarly, British Specification No. 980,110 discloses oxo-aluminum compounds having alkoxide group substituents which would make the products sensitive to hydrolysis and therefore affect stability of a surface coating composition containing a drying oil or resin if incorporated therein.

British Specification No. 767,585 discloses the use of compounds disclosed in British Specification No. 772480 in rendering fibrous materials water repellent.

Various proposals have been made to counter the increase in structure of a paint or varnish when certain organo aluminum compounds are added to media containing drying oils, alkyd resins or other resinous bodies with which the aluminum compounds can react.

U.S. Pat. Nos. 4,090,886 and 4,264,370 disclose a method for achieving the desirable characteristic of storage stability in air-drying compositions comprising an aluminum compound and a reactive paint medium in a mixture ratio which would normally prove to be unstable and cause gelation in the container before being applied to a surface. This is achieved by adding at least one mole, per mole of the aluminum compound, of certain labile monofunctional reactants, preferably a monohydroxy compound such as a lower alkanol. The labile monofunctional reactants will react preferentially to impede the complex association which occurs when aluminum compounds are added to drying oils or paint media containing reactive groups such as hydroxyl and carboxyl. It is assumed that in the presence of the labile reactant, an equilibrium is established which is disturbed when the film is applied to a surface whereby the labile reactant is released by hydrolysis or by its own volatility. The equilibrium may be represented as follows:

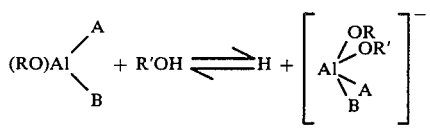

Oxo-aluminum compounds, however, do not readily complex with weak hydroxyl groups on alkyd resins. They do react slowly with the stronger carboxyl groups resulting in the undesirable formation of hydroxy-aluminum disoaps as shown in the foregoing, which cause surface coating media to thicken on storage.

Other patents relating to organoaluminum compounds are U.S. Pat. Nos. 2,744,074, 2,979,497, 3,198,332, 3,487,097, 4,055,634, 4,075,178, 4,132,724 and British Pat. Nos. 809,309, 888,666, 1,544,405 and Czech Pat. No. 85300. See also Mehrotra, "Aluminum Alkoxides," *J. Indian Chem. Soc.*, Vol. 30, No. 9, pages 585–591 (1953).

I have now found oxo-aluminum complexes which are suitable for use as coordination driers in surface coatings based on synthetic resins which are substantially free from the attendant disadvantages just described.

SUMMARY OF THE INVENTION

The present invention provides oxo-aluminum complexes of the formula $$O'_{a+1}(Al-X)_a(Al-OR_bX_{2-b})_2$$

wherein
- —OR is an alkoxy group in which R is an alkyl group containing from 1 to 4 carbon atoms or an alkoxyalkyl group containing 4 to 6 carbon atoms;
- X is a substituent derived by elimination of a hydrogen atom from an enolate or a mixture of substituents comprising at least one substituent derived by elimination of a hydrogen atom from an enolate and one or more substituents derived by elimination of a hydrogen atom from an alcohol containing more than 4 carbon atoms, a phenol, a carboxylic acid, a mono-ester of a dicarboxylic acid or a di-ester of a tri-carboxylic acid;
- O' is an oxygen atom which bridges two aluminum atoms;
- a is an integer of 2 or more; and
- b has the value of 0.5, 1, 1.5 or 2 with the proviso that $2b/a+2$ is less than 0.33.

The invention requires an excess of residual alkoxide which facilitates the polycondensation of the substituted and partially hydrolyzed aluminum alkoxide to a hydroxyl content approaching zero and results in a substantial residual alkoxide content. This is deemed to result in a significant stabilizing advantage for the products of the present invention over those of British Specification No. 907,558 and others discussed herein arising from the ability of the products of the present invention to react with alkyd resins containing reactive carboxyl groups without the by-product of —OH groups which are known to contribute to the instability of air drying compositions containing these ingredients, by thickening. The reaction may be simply represented as follows:

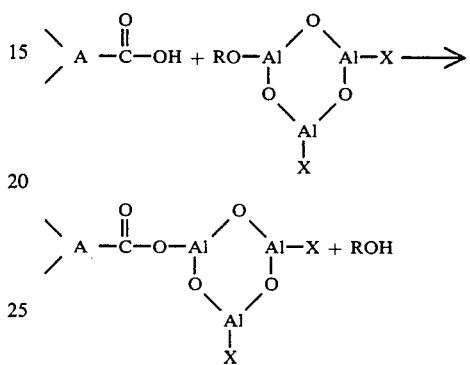

The limitation on the content of alkoxide groups in the complexes is essential because higher values are technically undesirable in that they would provide more alkoxide groups than needed to react with available reactive groups on the drying oil or resin without causing the formation of OH groups which could lead to thickening.

Further, an excess of available alkoxide groups would result in greater sensitivity to atmospheric or other sources of water causing hydrolysis which would thereby endanger stability.

The invention also provides air-drying compositions comprising a synthetic resin such as an alkyd resin and an aluminum complex or composition as defined above.

DESCRIPTION OF THE INVENTION

The substituent or substituents represented by X are selected in order that they may contribute valuable additional properties to the surface coatings in which the complexes of the invention are used. For example, the substituents may be beneficial in providing greater stability, lower viscosity/higher solids, more precise control of "wet edge" and hard dry time, controlled water absorption/water vapor permeability, improved pigment wetting, improved mechanical properties, increased durability and means of inhibiting ferrous metal corrosion.

According to the invention X represents a substituent derived by elimination of a hydrogen atom from an enolate or a mixture of substituents at least one of which is derived by elimination of a hydrogen atom from an enolate and one or more substituents derived by elimination of a hydrogen atom from an alcohol containing more than 4 carbon atoms, a phenol, a carboxylic acid, a mono-ester of a dicarboxylic acid or a di-ester of a tricarboxylic acid. Enolates as a general class of compounds are known to react with organo aluminum compounds and are used in surface coating compositions containing these compounds in order to impart certain valuable properties to the compositions such as water-resistance.

Typical examples of compounds from which the substituents represented by X can be derived to enable the aluminum complexes or compositions of the invention to be used in a wide range of surface coatings, which include air drying and low bake industrial coatings of all types, are enolate groups derived from ethyl or higher esters of acetoacetic acid, acetyl acetone or other $\beta$-diketones, diethyl malonate or other malonic esters and optionally substituents derived from butoxyethanol, cyclohexanol, ethylhexanol, Synperonic NX (a monoalkylphenyl ether of a polyethylene glycol), Cirrasol ALN-WF (the monocetyl ether of a polyethylene glycol), glycol mono esters, glycerol or other triol diesters, phenol, p-tert-butyl phenol, o-phenylphenol, 2,6-di-tert-butyl-4-methylphenol, pentachlorophenol, anacardol, monohydric phenols in which one or more hydrogen atoms in the benzene ring are replaced by alkyl, aryl, alkoxy, aryloxy, halide or nitro groups; saturated and unsaturated fatty acids, other primary, secondary and tertiary aliphatic acids, e.g. methacrylic, neopentanoic, Versatic (mixture of trialkylacetic acids having 9–11 carbon atoms), ethylhexoic; aromatic acids, e.g. benzoic, p-nitrobenzoic; monoesters of dicarboxylic acids, e.g. acid monobutyl maleate, acid monoethyl phthalate, acid monoisopropyl dodecyl succinate.

The substituent OR is preferably derived from an alcohol where R is an alkyl group containing from 1 to 4 carbon atoms or an alkoxyalkyl group containing from 4 to 6 carbon atoms. Preferred alcohols are isopropanol, 2-butanol and ethoxyethanol.

The complexes of the invention may be manufactured by, in a first stage, reacting an aluminum alkoxide with the desired compound or compounds from which the substituent X is derived and, in a second stage, condensing the resulting substituted aluminum intermediate compound by reaction with a molar deficiency of water; i.e., less than 1 mole of water per two alkoxide radicals. The alcohol by-product is removed by distillation. The water is preferably added to the reaction mixture as a water/alcohol solution or as water vapor.

In another aspect, the complex may be manufactured by, in a second stage, condensing the substituted aluminum intermediate compound by reaction with a deficiency of a carboxylic acid, such as less than one mole of the carboxylic acid for every two alkoxide radicals. The by-product alcohol displaced by the carboxylic acid is first removed by distillation to achieve the higher temperature desirable for the condensation reaction in which the substituted acyloxide and part of the residual alkoxide are released as ester and the >Al—O—Al< compound is formed. In a preferred embodiment, the carboxylic acid used is one in which the available alkoxide condenses to form a volatile ester which can be removed readily by distillation, that is, usually not containing more than 6 carbon atoms.

The method of manufacture of the compounds is further illustrated by reference to the following examples.

EXAMPLE 1

| (A) | Aluminum isopropoxide | 1224 g. |
|     | Ethyl acetoacetate    | 780 g.  |
| (B) | Water                 | 108 g.  |
|     | Isopropanol           | 108 g.  |
| (C) | Aluminum isopropoxide | 204 g.  |
|     | Ethyl acetoacetate    | 130 g.  |

The aluminum isopropoxide from (A) was heated to 120° C. to liquefy it, charged to a flask fitted with a stirrer, thermometer and condenser for refluxing and distillation, and cooled to 80° C. The ethyl acetoacetate from (A) was added slowly and the exothermic heat removed by allowing the by-product isopropanol to reflux. When the addition of the ethyl acetoacetate was completed the mixture was maintained under reflux for a further 30 minutes before cooling to 25°–30° C. The water/isopropanol solution (B) was then added slowly with stirring to maintain homogeneity and the mixture was heated under distillation conditions to remove the by-product isopropanol and effect condensation to the oxo compound.

When the temperature had reached 150° C. it was held for 1 hour at atmospheric pressure before adding the premixed composition (C) and continuing under distillation conditions at 150° C. for a further 1 hour.

The distillate of isopropanol contained some ethanol and approached the theoretical figure for complete condensation and distillation.

The product was diluted with white spirit to an aluminum content of 10%. It was a clear solution, pale yellow in color and had a viscosity of about 1.8 poises at 20° C.

EXAMPLE 2

| (A) | Aluminum triethoxyethoxide | 1176 g. |
|     | Ethoxyethanol              | 64 g.   |
|     | Ethyl acetoacetate         | 520 g.  |
| (B) | Versatic acid              | 175 g.  |
| (C) | Water                      | 54 g.   |
|     | Ethoxyethanol              | 54 g.   |

The aluminum triethoxyethoxide containing approximately 5.4% excess ethoxyethanol (A) was charged to a flask and stirring was commenced. The ethyl acetoacetate was added slowly and the resulting exothermic reaction raised the temperature to 97° C. where it was held for 30 minutes while the Versatic acid (B) was slowly added. The mixture (C) was then added slowly while the temperature of the mixture was raised under reflux in 20 minutes to 130° C. Then, after changing to distillation conditions, the temperature was slowly raised to 160° C. over 45 minutes and the distillate of ethoxyethanol was collected. Vacuum was applied to remove the final traces of ethoxyethanol and the combined distillate was weighed.

The yield of ethoxyethanol was 36 g. less than the theoretical yield. This may be attributed to some ester interchange resulting in the displacement of combined ethanol in ethyl acetoacetate by ethoxyethanol. Some ethanol and/or ethoxyethanol may be lost during the vacuum distillation storage.

The product was diluted with white spirit to an aluminum content of 8%. At this concentration it had a viscosity of about 60 cps at 25° C. and was a clear, pale yellow solution.

EXAMPLE 3

The product of Example 1 was prepared according to the process employed in Example 1 but was diluted to a 10% aluminum content with di-octyl maleate.

EXAMPLE 4 (COMPARATIVE)

| (A) | Aluminum isopropoxide | 1020 g. |
|---|---|---|
| | Ethyl acetoacetate | 650 g. |
| | Water | 90 g. |
| | Isopropanol | 90 g. |

The aluminum isopropoxide was charged to a flask and stirring was commenced. The ethyl acetoacetate was added slowly over a period of 20 minutes. The exothermic reaction during the addition caused the temperature in the flask to rise to about 95° C. Cooling water was applied to lower the temperature to 24° C. The water and isopropanol (A) was stirred in over a period of 30 minutes. After the addition of (A) the apparatus was arranged for distillation and heat was applied to the flask. Distillation was continued at atmospheric pressure until a temperature of 150° C. was reached. The product was cooled and was diluted to an 8% aluminum content with white spirit.

EXAMPLE 5

| (A) | Aluminum isopropoxide | 612 g. |
|---|---|---|
| | Versatic acid | 525 g. |
| | Linoleic acid | 852 g. |
| (B) | Aluminum isopropoxide | 204 g. |
| | Versatic acid | 175 g. |
| | Ethyl acetoacetate | 130 g. |

The aluminum isopropoxide from (A) was heated to 120° C. to liquefy it, charged to a flask and cooled to 70°–80° C. The Versatic acid from (A) was added slowly under distillation conditions. Heat was applied and the isopropanol distillate was collected. When the temperature had reached 150° C. the linoleic acid was added slowly and the further distillate of isopropanol was collected. Further heat was applied to raise the temperature slowly to 190° C. to complete distillation of by-product isopropanol. The temperature was then raised slowly to a maximum of 220° C. to effect condensation, mainly of linoleate with isoproxide, with the release of isopropyl linoleate as the principle by-product.

The product was cooled to 170° C. and the preformed product (B) was added to it without further heating until the temperature had dropped to 150° C. It was held at 150° C. for a further 30 minutes to complete distillation of the by-product isopropanol and the homogenization of the reaction complex. The product was then cooled.

The product was a clear, light-brown liquid having a viscosity of about 1 poise at 24° C. and an aluminum content of 5.3%.

EXAMPLE 6

| (A) | Aluminum isopropoxide | 1020 g. |
|---|---|---|
| | Ethyl acetoacetate | 325 g. |
| | Linoleic acid | 725 g. |
| | Water | 81 g. |
| | Isopropanol | 81 g. |

The process was the same as described in Example 4 with the exception that (A) was stirred into the reaction mixture at a temperature of 70°–80° C. The linoleic acid was introduced after the addition of the ethyl acetoacetate. The product was diluted to 6% aluminum content with white spirit.

The products of Examples 1, 2, 3 and 5 can be represented by the following general formulae:

EXAMPLE 1 AND 3

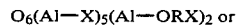

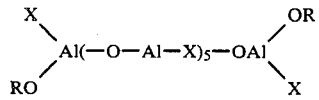

EXAMPLES 2 AND 5

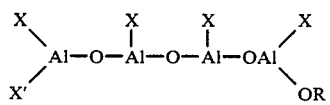

When the oxo-aluminum complexes of the invention are added to a synthetic resin solution, it has been found that the alkoxy group (—OR) on the complex reacts preferentially by direct addition with the available carboxyl or other reactive groups on the resin and effectively reduces the acid value of the resin. As previously discussed, with oxo-aluminum compounds which do not contain alkoxide substituents, reaction with carboxyl groups, which may be available on resins to which the oxo-aluminum compound is added, results in the carboxyl groups attacking the oxo-linkage with the formation of hydroxy aluminum di-soaps which contributes to storage instability of surface coatings manufactured using these compounds. In contrast, with the oxo-aluminum complexes of the present invention, the carboxyl groups on the resin are effectively neutralized by the alkoxy group of the oxo-aluminum complexes, thereby leaving the remaining active groups free to promote the drying mechanism through reaction with hydroperoxides and other groups resulting from the oxidation process on applying the coating to a surface.

It is important that sufficient alkoxy groups are available from the oxo-aluminum complex to neutralize substantially all the free carboxyl groups on the resin.

According to a particular embodiment of this invention, which is especially useful when resins of high initial acid value are used, the acid value of the resin can be reduced prior to adding the oxo-aluminum complexes of the invention. This is preferably achieved by esterifying the free carboxyl groups by a process of direct addition using an oxirane compound. Suitable oxirane compounds include ethylene oxide, propylene oxide, epichlorohydrin, methyl glycidyl ether, phenyl glycidyl ether, glycidyl ethyl hexoate, glycidyl Versatate, glycidyl hydroxide and epoxidized fatty esters.

To reduce acid value, one or more of these oxirane compounds is added to the resin solution in stoichiometric excess over the acid value of the resin and then heated under reflux conditions for a period of time which varies with the compound and with the excess used.

Before addition of the oxo-aluminum complexes to a resin medium, the product concentrate should be diluted at the end of the condensation stage to give the maximum viscosity consistent with easy handling of the material. This can be achieved using volatile solvents such as white spirit or non-volatile solvents, which are particularly useful in applications where a medium having a high non-volatile content is required. They can also contribute to the properties of the applied film. Particularly preferred non-volatile solvents include di-octyl maleate, di-butyl phthalate, di-nonyl fumarate, vinyl stearate, triphenyl phosphate and chlorinated paraffins.

It is preferable, although not essential, to add the resin solutions to the complexes of the invention. If the resin solution is of high viscosity, it may be preferable to reduce its viscosity by heating it before addition to the complex to improve miscibility and expedite the homogenization of the mix to preclude any localized cross-linking reactions which may occur where there is a deficiency of aluminum.

Table 1 shows the improved drying performances obtained when the complexes of Examples 1-6 were used to catalyze the drying of the commercially available alkyd resin medium Synolac 29W. Before addition of the complexes, the medium was diluted with white spirit to 62% non-volatile content and 0.06% cobalt was added as cobalt naphthenate based on the weight of the non-volatile alkyd. The tests were carried out three days after preparation of the drying media.

TABLE 1

| Example | Al %* | Viscosity (Poises) (24 hrs) | (28 days) | Drying Rate (Beck Koller) 1 | 2 | 3 | 4 | Condition of Film |
|---|---|---|---|---|---|---|---|---|
| 1 | 1 | 2.8 | 4.4 | 1.4 | 2.3 | 3.6 | 4.5 | Hard and glossy |
| 1 | 6 | 1.5 | 2.1 | 0.9 | 3.2 | 4.3 | 6.2 | Softer than 1/1 |
| 2 | 1 | 3.2 | 4.4 | 1.9 | 2.7 | 3.9 | 4.6 | Hard and glossy |
| 2 | 6 | 1.5 | 2.0 | 2.3 | 2.8 | 4.2 | 6.1 | Slightly softer than 2/1 |
| 3 | 1 | 3.1 | 4.6 | 2.2 | 2.8 | 3.4 | 4.1 | Hard and glossy |
| 3 | 6 | 2.6 | 3.3 | 3.0 | 3.6 | — | 4.2 | Hard and glossy |
| 5 | 1 | 2.8 | 3.7 | 2.0 | 2.5 | 3.4 | 4.2 | Hard and glossy |
| 5 | 6 | 2.4 | 3.2 | 2.4 | 2.8 | 3.4 | 3.8 | Slightly softer than 5/1 |
| 6 | 1 | 3.4 | 4.0 | 1.9 | 3.2 | 3.8 | 6.8 | Hard and glossy |
| 6 | 6 | 1.4 | 1.8 | 2.0 | 3.3 | 4.7 | 7.8 | Hard and glossy |
| Standard Co 0.06 Pb 0.5 Ca 0.25 | — | 3.4 | 4.9 | 2.4 | 5.4 | 8.8 | 13.4 | Persistent surface bite** |
| 4(Comparative) 1 | | 3.6 | 9.6 | 1.8 | 2.4 | 3.3 | 3.8 | Hard and glossy |
| 4(Comparative) 1 | | 3.1 | 16.2 | 1.5 | 2.4 | 3.6 | 4.0 | Hard and glossy |

*Al % based on non-volatile content of Synolac 29W.
**"Bite" means retention of a tendency to adhere when pressure is applied to the coating by the hand.

Table 2 shows the improved storage stability of air drying compositions prepared according to the invention using Synolac 29W when compared with a typical example of an air drying composition disclosed in U.S. Pat. No. 4,090,886, containing aluminum diethoxy ethoxide monoethylacetoacetate and ethoxyethanol—molar equivalent, and the product of Example 4.

TABLE 2

| Example | Al %* | Viscosity (poises) at 21 C. after (days) 1 | 10 | 17 | 24 | 31 | 42 |
|---|---|---|---|---|---|---|---|
| Comparative | 1 | 3.6 | 5.1 | 6.1 | 6.6 | 10.0 | 13.5 |
| | 6 | 2.1 | 4.4 | 7.0 | 10.7 | 25.0 | gelled |
| 1 | 1 | 2.8 | 3.2 | 3.5 | 4.0 | 4.5 | 4.8 |
| | 6 | 1.5 | 1.5 | 1.7 | 1.8 | 2.1 | 2.2 |
| 2 | 1 | 3.2 | 3.2 | 3.5 | 4.0 | 4.5 | 4.6 |

TABLE 2-continued

| Example | Al %* | Viscosity (poises) at 21 C. after (days) 1 | 10 | 17 | 24 | 31 | 42 |
|---|---|---|---|---|---|---|---|
| | 6 | 1.5 | 1.5 | 1.6 | 1.8 | 2.1 | 2.2 |
| 3 | 1 | 3.1 | 3.3 | 3.6 | 3.9 | 4.7 | 4.9 |
| | 6 | 2.6 | 2.7 | 2.7 | 3.1 | 3.4 | 3.4 |
| 5 | 1 | 2.8 | 2.9 | 3.2 | 3.6 | 3.8 | 3.9 |
| | 6 | 2.4 | 2.6 | 2.6 | 3.0 | 3.2 | 3.2 |
| 6 | 1 | 3.4 | 3.2 | 3.4 | 3.8 | 4.5 | 5.8 |
| | 6 | 1.4 | 1.5 | 1.5 | 1.8 | 1.8 | 2.0 |
| 4 (Comparative) | 1 | 3.6 | 5.4 | 6.1 | 8.2 | 10.4 | 70.0 |
| | 6 | 3.1 | 6.2 | 10.4 | 15.8 | 22.6 | slack gelled |

*Al% based on nonvolatile content of Synolac 29W.

Various changes and modifications of the invention can be made, and to the extent that such variations incorporate the spirit of this invention, they are intended to be included within the scope of the appended claims.

I claim:

1. An oxo-aluminum complex of the formula $$O'_{a+1}(Al-X)_a(Al-OR_bX_{2-b})_2$$

wherein

—OR is an alkoxy group in which R is an alkyl group containing from 1 to 4 carbon atoms or an alkoxyalkyl group containing 4 to 6 carbon atoms;

X is a substituent derived by elimination of a hydrogen atom from an enolate or a mixture of substituents comprising at least one substituent derived by elimination of a hydrogen atom from an enolate and one or more substituents derived by elimination of a hydrogen atom from an alcohol containing more than 4 carbon atoms, a phenol, a carboxylic acid, a mono-ester of a dicarboxylic acid or a di-ester of a tricarboxylic acid;

O' is an oxygen atom which bridges two aluminum atoms;

a is an integer of 2 or more; and b has the value of 0.5, 1, 1.5 or 2 with the proviso that 2b/a+2 is less than 0.33, wherein said oxo-aluminum complex has a substantial residual alkoxide content and a substantial absence of hydroxyl groups thereby resulting in a significant stabilizing effect.

2. An oxo-aluminum complex according to claim 1 having the formula

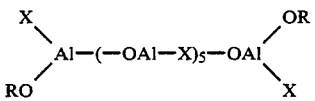

3. An oxo-aluminum complex according to claim 2 in which said R is isopropyl and said X is ethyl acetoacetyl.

4. An oxo-aluminum complex according to claim 1 having the formula

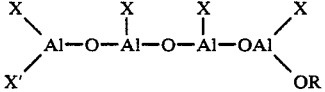

wherein X and X' are each a substituent derived by elimination of a hydrogen atom from an enolate or a mixture of substituents comprising at least one substituent derived by elimination of a hydrogen atom from an enolate and one or more substituents derived by elimination of a hydrogen atom from an alcohol containing more than 4 carbon atoms, a phenol, a carboxylic acid, a mono-ester of a dicarboxylic acid or a di-ester of a tricarboxylic acid.

5. An oxo-aluminum complex according to claim 4 in which R is isopropyl, X is Versatic and linoleic and X' is ethyl acetoacetyl.

6. An oxo-aluminum complex according to claim 4 in which R is ethoxyethyl, X is ethyl acetoacetyl and X' is Versatic.

7. An oxo-aluminum complex according to claim 1 in which said enolate is ethyl acetoacetate.

8. A method for preparing an oxo-aluminum complex according to claim 1, which comprises reacting, in a first stage, at least one aluminum alkoxide with at least one enolate and in a second stage, condensing the resulting aluminum intermediate compound by reaction with water or a carboxylic acid in a proportion of less than one mole of water or carboxylic acid per two moles of alkoxide radicals.

9. The method according to claim 8 in which said enolate is ethyl acetoacetate.

10. An air-drying composition comprising an oxo-aluminum complex according to claim 1 and a synthetic resin.

11. Air air-drying composition according to claim 10 wherein the synthetic resin is an alkyd resin.

12. The method according to claim 8 in which said aluminum alkoxide is reacted in the first stage, with said enolate and one or more compounds selected from alcohols containing more than 4 carbon atoms, phenols, carboxylic acids, mono-esters of dicarboxylic acids and di-esters of tricarboxylic acids.

* * * * *